US010722712B2

(12) United States Patent
Grosskopf et al.

(10) Patent No.: US 10,722,712 B2
(45) Date of Patent: Jul. 28, 2020

(54) SYSTEM FOR LOCATION-DEPENDENT THERAPY DELIVERY

(71) Applicant: BIOTRONIK SE & CO. KG, Berlin (DE)

(72) Inventors: Rainer Joerg Grosskopf, Portland, OR (US); Michael Reinert, Tigard, OR (US)

(73) Assignee: Biotronik SE & Co. KG, Berlin (DE)

( * ) Notice: Subject to any disclaimer, the term of this patent is extended or adjusted under 35 U.S.C. 154(b) by 97 days.

(21) Appl. No.: 15/725,312

(22) Filed: Oct. 5, 2017

(65) Prior Publication Data

US 2018/0110983 A1    Apr. 26, 2018

Related U.S. Application Data

(60) Provisional application No. 62/410,433, filed on Oct. 20, 2016.

(51) Int. Cl.
| | | |
|---|---|---|
| *A61N 1/00* | (2006.01) | |
| *A61N 1/36* | (2006.01) | |
| *A61N 1/372* | (2006.01) | |

(52) U.S. Cl.
CPC ..... *A61N 1/36034* (2017.08); *A61N 1/36062* (2017.08); *A61N 1/36146* (2013.01); *A61N 1/36167* (2013.01); *A61N 1/372* (2013.01); *A61N 1/37217* (2013.01); *A61N 1/37223* (2013.01); *A61N 1/37264* (2013.01)

(58) Field of Classification Search
CPC ............... A61N 1/36034; A61N 1/372; A61N 1/37264; A61N 1/37223; A61N 1/36062; A61N 1/36167; A61N 1/36146; A61N 1/37217; A61N 1/3607; A61N 1/36139; A61N 1/37211–37252; A61N 1/3787
See application file for complete search history.

(56) References Cited

U.S. PATENT DOCUMENTS

| | | |
|---|---|---|
| 5,891,180 A | 4/1999 | Greeninger et al. |
| 9,149,643 B2 | 10/2015 | Tahmasian et al. |
| 9,533,162 B2 | 1/2017 | Ter-Petrosyan et al. |
| 2005/0004622 A1 | 1/2005 | Cullen et al. |
| 2010/0137945 A1 | 6/2010 | Gadagkar et al. |
| 2010/0328049 A1* | 12/2010 | Frysz ................. A61N 1/08 340/10.51 |
| 2016/0022996 A1 | 1/2016 | Kaula et al. |
| 2016/0144167 A1 | 5/2016 | Bakker et al. |
| 2017/0106196 A1 | 4/2017 | Ter-Petrosyan et al. |

FOREIGN PATENT DOCUMENTS

WO    2016028399 A1    7/2015

* cited by examiner

*Primary Examiner* — Scott M. Getzow
(74) *Attorney, Agent, or Firm* — Laurence A. Greenberg; Werner H. Stemer; Ralph E. Locher

(57) ABSTRACT

A system for spinal cord stimulation, includes a stimulation device having a plurality of electrodes. The stimulation device is configured to deliver spinal cord stimulation via the electrodes according to a set of stimulation parameters. The stimulation device is further configured to store a plurality of different sets of stimulation parameters. The stimulation device is further configured to select one of the stored sets and to deliver spinal cord stimulation according to this selected set, when the stimulation device or a component of the system is located in proximity to an external activator associated with the selected set.

11 Claims, 1 Drawing Sheet

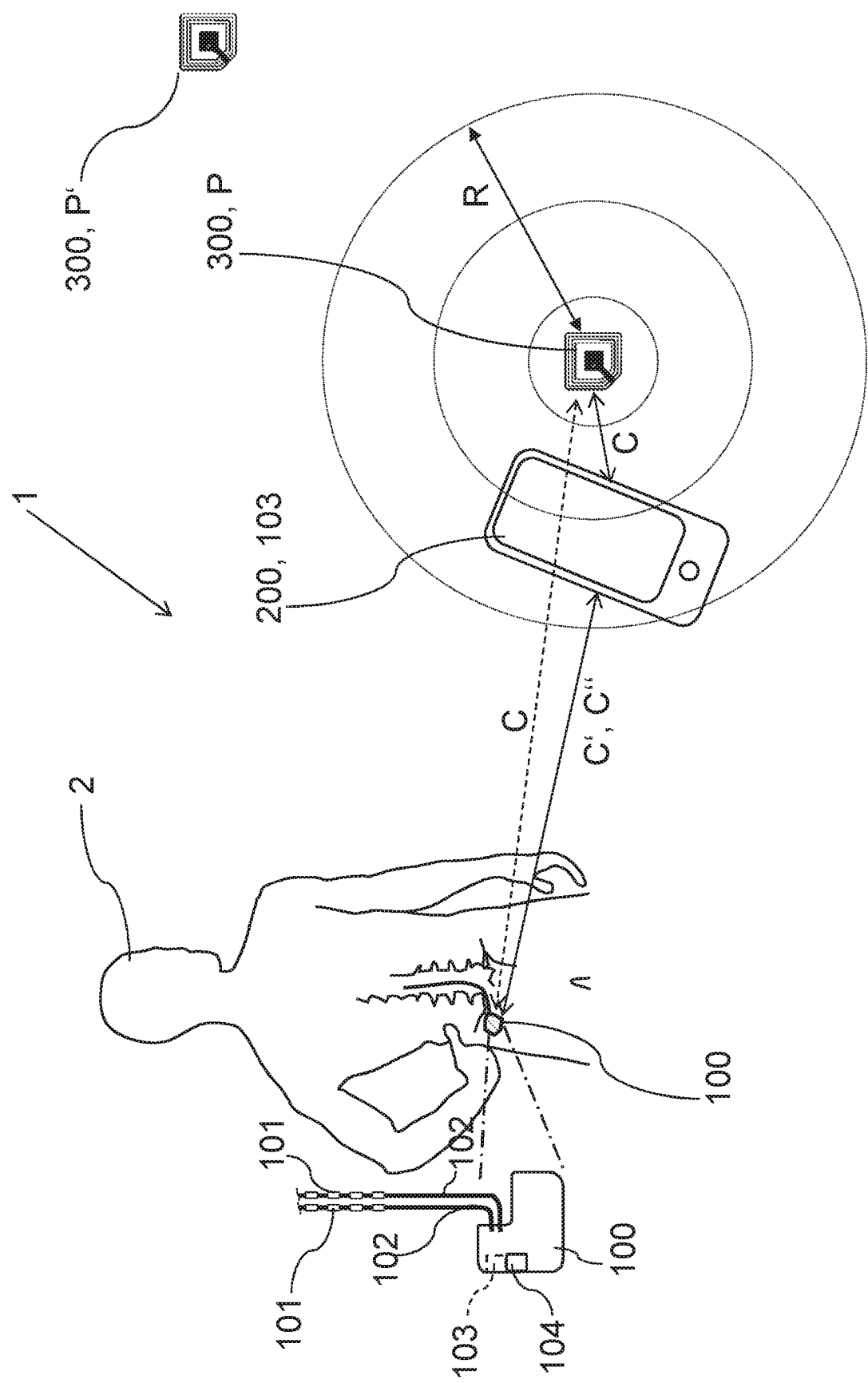

SYSTEM FOR LOCATION-DEPENDENT THERAPY DELIVERY

CROSS-REFERENCE TO RELATED APPLICATION

This application claims the priority, under 35 U.S.C. § 119(e), of U.S. Provisional Patent Application No. 62/410,433, filed Oct. 20, 2016; the prior application is herewith incorporated by reference in its entirety.

BACKGROUND OF THE INVENTION

Field of the Invention

The present invention relates to a system for providing spinal cord stimulation (SCS).

Spinal cord stimulators provide electrotherapy to reduce pain in patients. Patients frequently adjust the therapy or stimulation parameters in response to their current activities (e.g. sitting, standing, driving, walking, sleeping etc.).

International Publication WO 2016/028399, corresponding to U.S. Pat. No. 9,533,162 and U.S. Publication US 2017/0106196, discloses an SCS stimulation device, an external device and a patient remote control, wherein bidirectional communication between all devices via RF is possible.

Further, U.S. Publication US 2016/0022996 A1 describes a method for increasing the grade of automation in determination of SCS stimulation parameters (as thresholds for instance), wherein a 'sweep' process is disclosed, where the SCS device, for determining stimulation thresholds, automatically goes through every electrode, stimulates and requests patient feedback.

However, using hand-held remote controls to make the afore-stated adjustments can be a cumbersome process which may be too inconvenient in certain situations. Furthermore, a patient may be too impaired to use such remote control devices properly. These usability limitations leave the patient with less than optimal therapy in some situations.

SUMMARY OF THE INVENTION

It is accordingly an object of the present invention to provide a system for delivering SCS that is improved concerning the above described difficulty.

With the foregoing and other objects in view there is provided, in accordance with the invention, a system for spinal cord stimulation, comprising a stimulation device having a plurality of electrodes, wherein the stimulation device is configured to deliver spinal cord stimulation via the electrodes according to a set of stimulation parameters, wherein the stimulation device is further configured to store a plurality of different sets of stimulation parameters, and wherein the stimulation device is further configured to select one of the stored sets and to deliver spinal cord stimulation according to this selected set, when the stimulation device or a component of the stimulation system is located in proximity to an external activator associated with the selected set.

In an embodiment of the present invention, the stimulation device may include one or even two elongated flexible carriers, wherein each carrier includes a plurality of electrodes at a distal portion via which SCS may be applied to the spinal cord. Particularly, electrodes of one carrier may act as anodes wherein electrodes of the other carrier may act as cathodes. The two carriers particularly extend along one another.

Being located in proximity to an external activator particularly means that the stimulation device or the component is close enough to the external activator that the stimulation device/component can properly interact with the external activator so that the latter can be detected by the stimulation device/the component. Particularly, depending on the technology that is used, the notion proximity particularly means that a distance between the stimulation device/component is below a pre-definable threshold. Particularly, a typical distance lies within the range from 0.01 meters to 0.5 meters.

Particularly the stimulation device is formed as an implantable pulse generator (IPG). Possible external activators will be described in further detail below.

According to an embodiment of the present invention, the component is an external (particularly non-implantable) component that is configured to be disposed and/or used by the patient outside the patient's body.

However, the component can also be an implantable component that is implanted into the patient and particularly communicates with the stimulation device so as to e.g. transmit data identifying a set of stimulation parameters that is to be used.

Particularly, according to an embodiment of the present invention, the component is configured to transmit control signals to the stimulation device particularly via a line link or in a wireless fashion for operating/controlling the stimulation device.

Particularly, according to an embodiment of the present invention, the stimulation device includes a detecting unit for detecting the respective external activator. Further, in an embodiment, the detecting unit is configured to detect an electromagnetic signal from the respective external activator identifying a set of stimulation parameters associated with the respective external activator. Furthermore, in an embodiment, the stimulation device is configured to select the set of stimulation parameters identified by the electromagnetic signal and to conduct spinal cord stimulation using the set of stimulation parameters.

Alternatively, according to an embodiment, the component includes the detecting unit for detecting the respective external activator. Further, in an embodiment, the detecting unit is configured to detect an electromagnetic signal from the respective external activator identifying a set of stimulation parameters associated with the respective external activator. Furthermore, according to an embodiment, the component is configured to communicate data (particularly via a line link or in a wireless fashion) to the stimulation device, which data identifies the set of stimulation parameters. Furthermore, in an embodiment, the stimulation device is configured to select the set of stimulation parameters identified by the data and to conduct spinal cord stimulation using the set of stimulation parameters.

Further, according to an embodiment of the present invention, the component is one of: a remote control for operating the stimulation device, a hand-held device, a smart-phone, a smart watch, an object configured to be worn by the patient, a bracelet, a ring, a pair of spectacles, or a key fob. Further, the remote control may also be formed by any of the above listed devices, e.g. particularly by a smart phone or a smart watch. Particularly, in the framework of the present invention, a smart phone is a cell phone that includes a display, particularly in the form of a touchscreen, and a microprocessor, and is capable of executing software applications that are installed in a memory on the phone. Likewise, particularly, a smart watch is a watch that includes a display, particularly in the form of a touchscreen, and a microprocessor, and is capable of executing software applications that are installed in a memory on the watch. Moreover, the smartphone may maintain a direct or indirect wireless communication link to the stimulation device.

Further, according to an embodiment of the present invention, the stimulation system includes at least one external activator (or a plurality of such activators) that is configured to be placed in a patient's surrounding and is associated with a specific set of stimulation parameters of the stimulation device. In this way, a specific set of stimulation parameters can be selected with help of an external activator.

Furthermore, according to an embodiment, the respective external activator can be a passive tag (i.e. does not include a power supply but uses energy transmitted to the tag for processing and/or transmitting data) or an active tag (e.g. a tag that includes its own power supply for processing and/or transmitting data), and is particularly configured to communicate identification data identifying a specific set of stimulation parameters associated with the respective activator via an electromagnetic signal.

Particularly, different radio signal transmission standards may be used for the communication between the external activator and the stimulation device or the component, such as NFC, Bluetooth, Wi-Fi etc.

According to a preferred embodiment of the present invention, the respective external activator is an RFID tag, particularly a passive RFID tag.

Furthermore, according to an embodiment of the present invention, the stimulation parameters of the respective set of stimulation parameters are one, several or all of the following stimulation parameters:
- stimulation amplitude
- stimulation pulse width
- stimulation frequency and/or stimulation cycles
- electrode or electrodes for stimulation from a plurality of electrodes, e.g. selection of one or more electrodes from an array of electrodes.

In the context of the present invention, the term stimulation cycle should be understood as a recurring timing configuration of stimulation titration within a certain time frame as for instance minutes, hours, days or the like.

Furthermore, the stimulation device may additionally include one or several further sensors, particularly at least one of:
- an accelerometer,
- a temperature sensor,
- a pressure sensor or another sensor for measuring a signal representing a biological, biochemical and/or biophysical signal of the patient.

Furthermore, an external activator according to the present invention can also be any other device that uses communication via radio signals (particularly in the range from 2,402 GHz to 2,480 GHz, e.g. using Bluetooth and/or NFC) that can be detected by the detecting unit described above.

Particularly, in an embodiment, an external activator may be formed by a radio disposed in a motor vehicle. Here, when the component (e.g. a smart phone) or the stimulation device itself detects the radio (that e.g. uses Bluetooth to communicate with other devices in its proximity) the stimulation device will select the set of stimulation parameters appropriate for driving the motor vehicle.

Further, according to an embodiment, an external activator can also be formed by a satellite navigation system (e.g. GPS). Here, the component's capability of using such signals to determine the position of the component (e.g. smart phone etc.) is used to distinguish between different places (e.g. home and office, etc.)

Here, the patient can particularly setup location-based therapy rules, i.e., sets of stimulation parameters associated with each different place, on the component (e.g. smart phone) manually.

Further, in an embodiment, the component (e.g. smart phone) is configured to monitor adjustments made by the patient via the component (e.g. smart phone), e.g. to monitor which sets of stimulation parameters are used at specific places, and to deduce location-based rules, which are then applied automatically by the stimulation device.

Other features which are considered as characteristic for the invention are set forth in the appended claims.

Although the invention is illustrated and described herein as embodied in a system for location-dependent therapy delivery, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

The single FIGURE of the drawing shows a schematic representation of a system for spinal cord stimulation according to the present invention.

DETAILED DESCRIPTION OF THE INVENTION

Referring now to the FIGURE of the drawing in detail, there are seen embodiments of a system 1 for spinal cord stimulation according to the present invention.

Usually, patients 2 use a component 200 such as a remote control (e.g. in the form of a smart phone) throughout the day in order to adjust proper stimulation parameters for the spinal cord stimulation (SCS) for activities such as sitting (e.g. at a desk), or walking, or driving a car. Also, stimulation during the day may be different from stimulation during night time, etc. For operating an SCS stimulation device 100 patients may use a component 200 such as a smart phone 200 or an actual remote control when less familiar with a touch screen/smart phone. However, in certain situations handling and operating of such an operating device is difficult, for instance when waking up with the eyes still adapted to darkness or when being involved with other activities such as driving a car, etc.

Here, the present invention allows a location-dependent operating of the stimulation device that can be accomplished by the patient in an easy manner.

For this purpose, as shown in the FIGURE, a system 1 for SCS includes a stimulation device 100 having a plurality of electrodes 101, wherein the stimulation device 100 is configured to deliver spinal cord stimulation via the electrodes 101 according to a set P, P' of stimulation parameters.

Particularly, the stimulation device may include two flexible carriers 102 for carrying the electrodes 101, which carriers 102 may get tunneled during implantation to the vicinity of the stimulation device (e.g. an implantable pulse generator or IPG) 100 that is typically implanted subcutaneously in the patient's lower abdominal or gluteal region. The carriers 102 may terminate proximally in connectors that are then inserted into the IPG 100 header to allow conducting electrical charge to the electrodes 101. However, any other stimulation device construction may also be used. Further, the position-dependent therapy delivery described here may also be used in conjunction with other medical devices.

Further, particularly, the stimulation device 100 is configured to store a plurality of different sets P, P' of stimulation parameters (e.g. in a semiconductor memory 104), wherein the stimulation device 100 is further configured to select one of the stored sets P, P' and to deliver spinal cord stimulation according to this selected set, when the stimulation device 100 or the component 200 (e.g. a remote control in the form of a smart phone) of the system 1 is located in proximity to an external activator 300 associated to the selected set.

In one example according to the present invention, the external activator 300 may be associated with parameter settings that provide pain therapy in the lower back. Such an external activator may be placed at the patient's work station. According to another example, an external activator 300 may be associated with parameter settings that provide pain therapy in the legs. In this case, the external activator may be placed at the patient's bedside. In another example for the present invention, an external activator 300 may be associated with parameter settings that provide no pain therapy, e.g. for providing an option for turning off the stimulation. Such an external activator 300 may be placed at the patient's bedside as well. The three examples for external activators allow the patient to switch between three preconfigured parameter sets by e.g. placing a smartphone in proximity of one of the external activators.

In the following, an embodiment of the present invention will be described in which the component 200, here—as an example—in the form of a smart phone 200, is used to detect the individual external activator 300. However, a detecting unit 103 for detecting such an external activator 300 may also be integrated into the implanted stimulation device 100 itself which then communicates via radio signals C (dashed double arrow in FIG. 1) with the respective activator 300 directly such that the component 200 is not needed for detecting activators 300 and selecting corresponding stimulation parameter sets P, P'.

Particularly, apart from detecting external activators 300, e.g. by using an integrated detecting unit 103 which may be provided by some radio communication functionality of the smart phone 200 (e.g. Bluetooth, NFC etc.), the component/smart phone 200 may also be configured to transmit control signals C" to the stimulation device 100 for operating the stimulation device 100, e.g. for adjusting stimulation parameters manually. Thus, the function of the component can be twofold. One the one hand it functions as an ordinary remote control of the stimulation device 100 and on the other hand it is used to detect the external activators 300.

Particularly, the individual external activator 300 can be a simple (e.g. passive) RFID tag 300 that is placed by the patient 2 at a certain location in the surroundings of the patient 2, where a specific set of stimulation parameters P, P' shall be used for delivering SCS by the implanted stimulation device 100.

For instance, such external activators 300/RFID tags 300 may be placed by the patient 2 on a nightstand, on a desk, near a bed, in a bathroom, near a couch or in the car, wherein each activator 300 is assigned to a different set of stimulation parameters that shall be used at the specific location. Particularly, the patient 2 may also carry such activators 300 (e.g. on a key chain), namely one for each pre-configured set of stimulation parameters, for easy programming of the stimulation device 100 without the use of a touchscreen or the like.

When different tags 300 corresponding to different sets P, P' of stimulation parameters are placed at specific locations, as indicated in the FIGURE, the patient 2 can select a specific set P, P' by placing the component 200 (e.g. smart phone or any other remote control or object having the specific functionality as described herein) in the proximity R (e.g. a 5 cm radius around the tag 300) of the respective tag 300 as shown in the FIGURE, where the set P has been chosen by the patient 2.

The component 200 then detects an electromagnetic signal C from the respective external activator 300 (e.g. via Bluetooth, NFC or any other suitable radio communication standard) identifying the set of stimulation parameters P assigned to the external activator 300. The component 200 then transmits corresponding data C' to the stimulation device 100, which data C' identifies the corresponding set of stimulation parameters P. The stimulation device 100 is configured to receive this data C' and to select the set of stimulation parameters P among the sets P, P' stored in its memory 104. Then, the stimulation device 100 will deliver SCS therapy using the selected set P of stimulation parameters until another set is selected by the user (or the user decides to alter SCS manually via the component 200).

In this way, the user interaction is reduced from having to push several buttons or perform several operations on a touchscreen of a remote control 200 to simply placing the component 200 in a special location in the proximity R of a tag 300.

Concerning the radio communication between the tags 300 and the component 200, NFC is suitable for very close proximity awareness, while other radio technologies like Wi-Fi, RFID, and Bluetooth may provide more coarse location awareness.

Particularly, proximity to a car's Bluetooth-enabled radio may be used to configure the implant 100 with settings appropriate while driving. Further, GPS-based location awareness can be used by the system 1 to distinguish if the patient 2 is at home or at work.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. A system for spinal cord stimulation, the system comprising:
   at least one external activator comprising identification data identifying a specific set of stimulation parameters; and
   a stimulation device having a plurality of electrodes, said stimulation device being configured to deliver spinal cord stimulation via said electrodes according to said specific set of stimulation parameters, said stimulation device being further configured to store a plurality of different sets of stimulation parameters, and said stimulation device being further configured to select said specific set of stimulation parameters from said plurality of stored sets and to deliver spinal cord stimulation according to said selected specific set, when said stimulation device or a component of the system communicates with said at least one external activator, each external activator of said at least one external activator comprising identification data identifying only one specific set of stimulation parameters of said plurality of different sets of stimulation parameters, and said stimulation device configured to select only said one specific set of stimulation parameters identified by a respective external activator when communicating with the respective external activator.

2. The system according to claim 1, wherein said component is an external component.

3. The system according to claim 1, wherein said component is configured to transmit control signals to said stimulation device for operating said stimulation device.

4. The system according to claim 1, wherein said stimulation device includes a detecting unit for detecting said external activator.

5. The system according to claim 4, wherein said detecting unit is configured to detect an electromagnetic signal from said external activator identifying the set of stimulation parameters comprised in said external activator, and said stimulation device is configured to select the set of stimulation parameters identified by said electromagnetic signal and to conduct spinal cord stimulation using said set of stimulation parameters.

6. The system according to claim 1, wherein said component includes a detecting unit for detecting said external activator, said detecting unit being configured to detect an electromagnetic signal from said external activator identifying the set of stimulation parameters comprised in said external activator, said component being configured to communicate data to said stimulation device identifying said set of stimulation parameters, and said stimulation device being configured to select said set of stimulation parameters identified by said data and to conduct spinal cord stimulation using said set of stimulation parameters.

7. The system according to claim 1, wherein said component is one of: a remote control for operating said stimulation device, a hand-held device, a smart-phone, a smart-watch, an object configured to be worn by a patient, a bracelet, a ring, a pair of spectacles, or a key fob.

8. The system according to claim 1, wherein said at least one external activator is a plurality of external activators, each identifying only a specific set of stimulation parameters of said plurality of sets stored by the stimulation device.

9. The system according to claim 1, wherein said external activator is a passive tag or an active tag.

10. The system according to claim 9, wherein said external activator is an RFID tag.

11. The system according to claim 1, wherein the stimulation parameters of the set of stimulation parameters are one, a plurality or all of the following stimulation parameters:
   stimulation amplitude;
   stimulation pulse width;
   at least one of stimulation frequency or stimulation cycles; or
   an electrode or electrodes for stimulation from a plurality of electrodes.

* * * * *